(12) United States Patent
Slurink

(10) Patent No.: US 9,738,459 B2
(45) Date of Patent: Aug. 22, 2017

(54) ADJUSTING SPACES BETWEEN ELECTRONIC CIGARETTE TUBES

(71) Applicant: Sluis Cigar Machinery B.V., Kampen (NL)

(72) Inventor: Oscar Slurink, Heino (NL)

(73) Assignee: Sluis Cigar Machinery B.V., Kampen (NL)

(*) Notice: Subject to any disclaimer, the term of this patent is extended or adjusted under 35 U.S.C. 154(b) by 0 days.

(21) Appl. No.: 15/309,548

(22) PCT Filed: May 12, 2015

(86) PCT No.: PCT/NL2015/050337
§ 371 (c)(1),
(2) Date: Nov. 8, 2016

(87) PCT Pub. No.: WO2015/174836
PCT Pub. Date: Nov. 19, 2015

(65) Prior Publication Data
US 2017/0158436 A1    Jun. 8, 2017

(30) Foreign Application Priority Data
May 16, 2014  (NL) ..................... 2012832

(51) Int. Cl.
*A24F 47/00* (2006.01)
*B65G 47/08* (2006.01)
(Continued)

(52) U.S. Cl.
CPC .............. *B65G 47/846* (2013.01); *A24C 5/00* (2013.01); *A24F 47/008* (2013.01); *A61M 15/06* (2013.01); *B65G 29/00* (2013.01); *B65G 47/088* (2013.01)

(58) Field of Classification Search
CPC .................................................. B65G 47/088
See application file for complete search history.

(56) References Cited

U.S. PATENT DOCUMENTS 3,567,043 A    3/1971  Sirvet et al.
3,802,364 A *  4/1974  Paramonoff ........... B21D 43/18
                                                     413/45

(Continued)

FOREIGN PATENT DOCUMENTS

DE          29708849 U1    9/1998
EP           0608824 A1    8/1994
WO        2011/040810 A1   4/2011

*Primary Examiner* — Thomas Randazzo
(74) *Attorney, Agent, or Firm* — Hoffmann & Baron, LLP

(57) ABSTRACT

An electronic cigarette tubes individualizer apparatus individualizes tubes received from a first track without spacing and provides the tubes to a second track with a spacing. The apparatus includes a rotary carrousel configured to rotate about a rotation axis and provided with a guide extending with the longitudinal axis partially along a line substantially intersecting the rotation axis; a stationary cam track extending around the rotation axis; a carriage mounted to the carrousel for traveling in a reciprocating movement along the guide driven by a cam follower following the cam track while the carrousel is rotating; and a receiver connected to the carriage for receiving the tube from the first track close to the rotation axis and delivering the tube to the second track further away from the rotation axis with a pitch.

17 Claims, 6 Drawing Sheets

(51) Int. Cl.
*B65G 47/84* (2006.01)
*A61M 15/06* (2006.01)
*A24C 5/00* (2006.01)
*B65G 29/00* (2006.01)

(56) References Cited

U.S. PATENT DOCUMENTS

| | | | | |
|---|---|---|---|---|
| 4,305,816 | A * | 12/1981 | Flood | B07C 5/126 |
| | | | | 209/549 |
| 5,979,634 | A * | 11/1999 | Odegard | B65G 47/252 |
| | | | | 198/408 |
| 7,114,535 | B2 * | 10/2006 | Hartness | B67C 3/02 |
| | | | | 141/1 |
| 9,580,253 | B2 * | 2/2017 | Papsdorf | B65G 47/082 |

* cited by examiner

ADJUSTING SPACES BETWEEN ELECTRONIC CIGARETTE TUBES

CROSS-REFERENCE TO RELATED APPLICATIONS

This application is the National Stage of International Application No. PCT/NL2015/050337 filed May 12, 2015, which claims the benefit of Netherlands Application No. NL 2012832, filed May 16, 2014, the contents of which is incorporated by reference herein.

FIELD OF THE INVENTION

The invention relates to an electronic cigarette tubes spacing adjustment apparatus for adjusting spaces between tubes received from a first track with a first spacing and delivered to a second track with a second spacing.

BACKGROUND OF THE INVENTION

In a fabrication process of an electronic cigarette it may be necessary to adjust spaces between electronic cigarette tubes on a track so that fabrication steps may be performed on the tubes. The stock of tubes may be fed to the first track where the tubes are provided, tube against tube, without spacing via a channel. To perform fabrication steps to the tubes the tubes may need to be individualised. After the fabrication steps the individual tubes may need to be grouped, tube against tube, for storage again.

SUMMARY OF THE INVENTION

It is an objective to provide an electronic cigarette tubes spacing adjustment apparatus for adjusting spaces between tubes received from a first track with a first spacing and delivered to a second track with a second spacing.

Accordingly there is provided an electronic cigarette tubes spacing adjustment apparatus for adjusting spaces between tubes received from a first track with a first spacing and delivered to a second track with a second spacing, wherein the apparatus comprises:

a rotary carrousel configured to rotate about a rotation axis and provided with a guide extending with the longitudinal axis partially along a line substantially intersecting the rotation axis;

a stationary cam track extending around the rotation axis;

a carriage mounted to the carrousel for traveling in a reciprocating movement along the guide driven by a cam follower following the cam track while the carousel is rotating; and, a receiver connected to the carriage for receiving the tube from the first track at a first distance from the rotation axis and delivering the tube to the second track at a second distance from the rotation axis while adjusting the spacing from the first spacing to the second spacing between delivering and receiving the tube.

By receiving the tube at a first distance from the rotation axis, rotating it with the carrousel while moving it with the carriage along the guide driven by a cam follower and delivering the tube to the second track at a second distance from the rotation axis the spacing between the tubes on the second track may be adjusted.

The term tube may be interpreted as a hollow cylinder, with optionally one of it ends closed.

According to a further embodiment the stationary cam track is provided in a plane substantially perpendicular to the rotation axis.

During the rotation of the carousel the cam follower therefore may follow the cam track.

According to an embodiment the guide may be provided in a plane substantially perpendicular to the rotation axis.

The guide therefore allows for movement in directions substantially perpendicular to the rotation axis.

According to a further embodiment the receiver is constructed and arranged to press the tube against a press wall.

The press wall provides sufficient guidance for the tube to clamp the tube between the press wall and the receiver.

According to a further embodiment the cam follower comprises a rotary wheel.

In this way a low friction movement of the cam follower through the stationary cam track is assured.

According to an embodiment the first or second track comprises a rotary carrousel.

The carrousel may take the tubes over from the rotary carousel and keep the distance between the tubes constant. Further fabrication steps may be performed on the individual tubes in the carrousels.

According to a further embodiment the first or second track comprises a channel with channel walls for guiding the tubes.

The channel walls may provide for a good guidance of the tubes to the rotary carrousel.

According to an embodiment the apparatus is constructed and arranged to transport the tubes with their longitudinal axis parallel to the rotation axis.

In this way the distance between the tubes may be adjusted by the apparatus.

According to an embodiment the guide extends between 2 to 25 cm from the rotation axis with the longitudinal axis along lines substantially intersecting the rotation axis.

The length of the guide and the form of the stationary cam track defines the stroke of the carriage which correlates to the spacing between the tubes which is created.

According to an embodiment between the guide and the carriage a linear bearing is provided.

In this way a low friction movement of the carriage over the guide is assured.

According to an embodiment the guide comprises a rail and the carriage is provided with a slide running over the rail.

In this way a low friction movement of the carriage over the rail is assured.

According to an embodiment between 5 to 100, preferably 10 to 50, and most preferably 20 to 40 guides with carriages are provided to the apparatus.

The productivity of the apparatus may be increased by providing multiple guides with carriages to the apparatus.

According to a further embodiment there is provided an apparatus, wherein the apparatus is constructed to receive the tubes with the first spacing smaller than the second spacing with which the tubes are delivered.

According to an embodiment there is provided an apparatus, wherein the apparatus is constructed to receive the tubes with the first spacing larger than the second spacing with which the tubes are delivered.

According to a further embodiment there is provided a method for adjusting spaces between electronic cigarette tubes, the method comprising:

rotating around a rotation axis a rotary carrousel provided with a guide extending with the longitudinal axis partially along a line substantially intersecting the rotation axis;

driving carriages reciprocating along the guide by a cam follower following a stationary cam track;

receiving tubes from a first track with a first spacing between the tubes with a receiver connected to the carriage from a first track at a first distance from the rotation axis; and delivering the tubes to a second track with a second spacing between the tubes at a second distance from the rotation axis.

By receiving the tube at a first distance from the rotation axis, rotating it with the carrousel while moving it with the carriage along the guide driven by a cam follower and delivering the tube to the second track at a second distance from the rotation axis the spacing between the tubes on the second track may be adjusted.

By receiving the tubes at a first distance close to the rotation axis, moving it with the carriage along the guide driven by a cam follower and delivering the tube to the second track further away from the rotation axis there is provided more spacing between the tubes on the second track.

By receiving the tubes at a first distance further away from the rotation axis, moving it with the carriage along the guide driven by a cam follower and delivering the tube to the second track at a second distance closer to the rotation axis there is provided less space between the tubes on the second track than on the first rack.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF THE INVENTION

Figure 1:
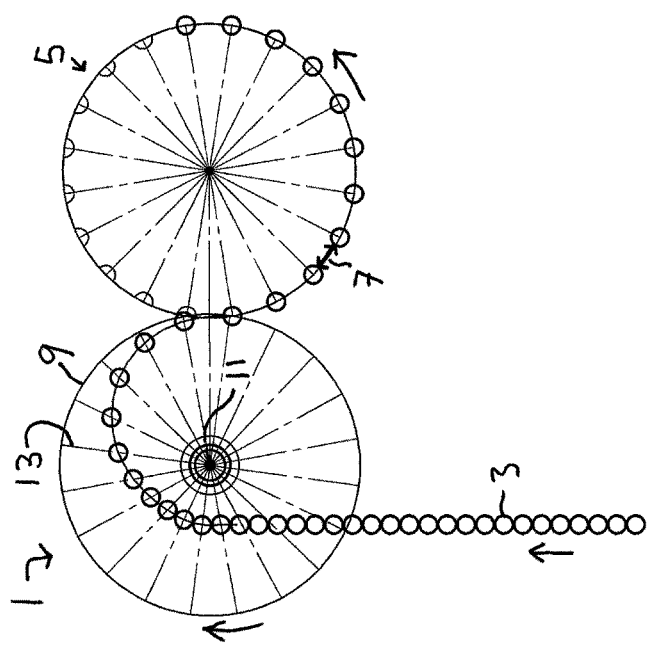
FIG. 1 depicts schematically a top view on an electronic cigarette tubes spacing adjustment apparatus.

FIG. 1 depicts schematically a top view on an electronic cigarette tubes spacing adjustment apparatus. The apparatus 1 adjusts spaces between tubes 3 received from a first track with a first spacing and delivered to a second track 5 with a second spacing 7. For example, the apparatus 1 individualises tubes 3 received from a first track without spacing and provided to a second track 5 with the second spacing 7. The first or second track may comprise a rotary carrousel. The rotary carrousel of the second track 5 may take the tubes over from the rotary carousel 9 and keeps the distance between the tubes constant. Further fabrication steps may be performed on the individual tubes in the rotary carousel of the second track 5. The apparatus 1 comprises a rotary carrousel 9 configured to rotate about a rotation axis 11 and provided with a guide extending with the longitudinal axis partially along a line 13 substantially intersecting the rotation axis 11.

Figure 2:
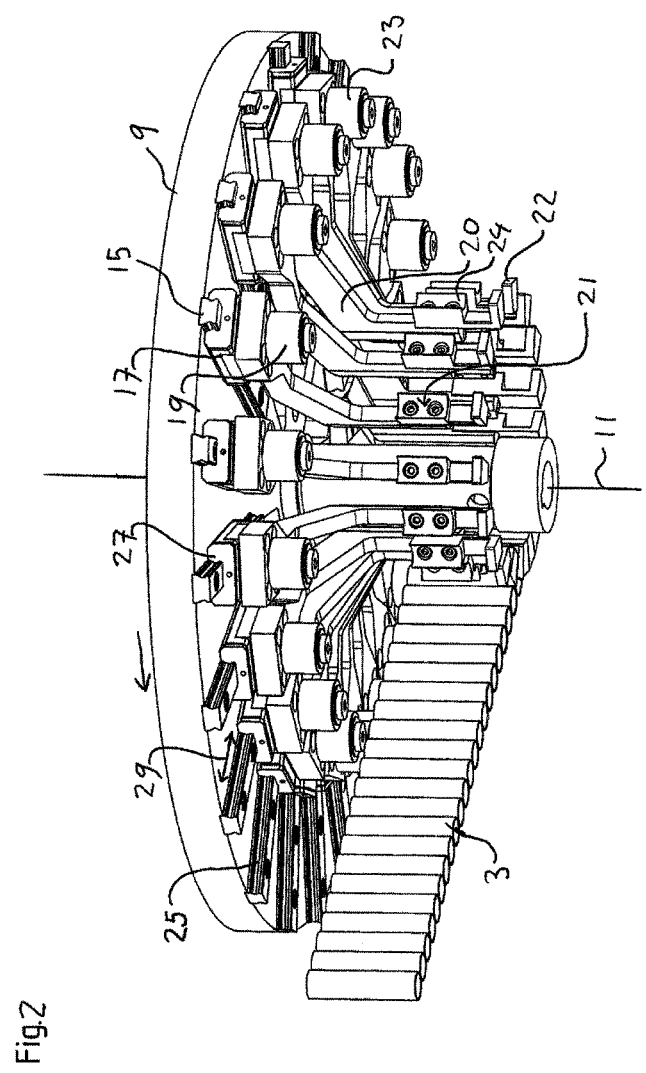
FIG. 2 depicts a side view of a portion of the adjustment apparatus.

FIG. 2 depicts a side view of a portion of the adjustment apparatus. The apparatus comprises the rotary carrousel 9 configured to rotate about the rotation axis 11 and is provided with a guide 15 extending with the longitudinal axis partially along the line substantially intersecting the rotation axis 11.

A carriage 17 may be movably mounted to the carrousel for traveling along the guide 15 in a reciprocating movement driven by a cam follower 19 following a cam track while the carousel 9 is rotating 5 to 100, preferably 10 to 50, and most preferably 20 to 40 guides 15 with carriages 17 are provided to the apparatus. The productivity of the apparatus may be increased by providing multiple guides with carriages to the apparatus.

A receiver 21 may be provided to the apparatus for receiving the tube 3 with a first spacing (e.g. zero) from the first track at a first distance (e.g. close) from the rotation axis 11 and delivering the tube to the second track at a second distance (e.g. further away) from the rotation axis with a second spacing (e.g. larger than zero). The receiver 21 is connected to the carriage 17 via an arm 20. The receiver may have a support 22 for supporting the tube and a contact portion 24 for contacting and directing the tube. The contact portion 24 may be provided with a flexible material. The tubes 3 are transported with their longitudinal axis parallel to the rotation axis 11. In this way the distance between the tubes may be adjusted by the apparatus.

The cam follower 19 may be a rotary wheel 23 in this way a low friction movement of the cam follower 19 over the stationary cam track is assured.

The guide 15 may be provided in a plane substantially perpendicular to the rotation axis 11 to allow for movement in directions substantially perpendicular to the rotation axis 11. The guide 15 may extend along the longitudinal axis along lines substantially intersecting the rotation axis 11 starting from 2 to 10 cm from the rotation axis 11 and ending 15 to 25 cm from the rotation axis 11. The length of the guide 15 and the form of the stationary cam track defines the reciprocating movement 29 of the carriage 17 which correlates to the spaces between the tubes. Between the guide 15 and the carriage 17 a linear bearing may be provided to assure a low friction movement of the carriage over the guide. The guide 15 may be a rail 25 and the carriage may be a slide 27 running with low friction over the rail in the reciprocating direction 29.

Figure 3:
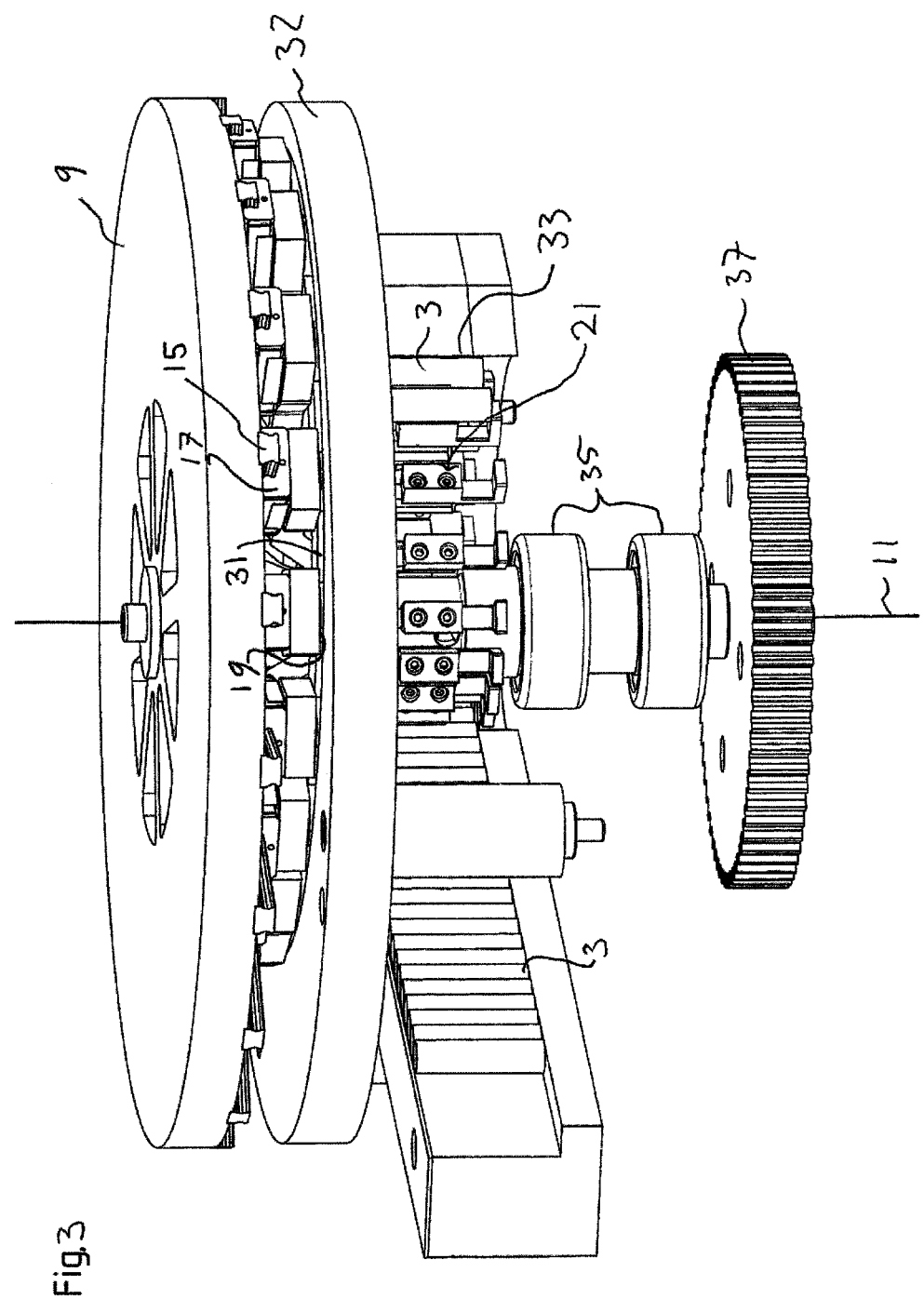
FIG. 3 depicts a side view on the adjustment apparatus.

FIG. 3 depicts a side view on the adjustment apparatus. The figure depicts the rotary carrousel 9 configured to rotate about the rotation axis 11, the guide 15 which is guiding the carriage 17 and the receiver 21 for receiving the tube 3.

The apparatus is further provided with a stationary cam track 31 extending around the rotation axis 11. The stationary cam track 31 is provided in a cam track portion 32 and is followed by the cam follower 19. The stationary cam track 31 is provided in a plane substantially perpendicular to the rotation axis 11 so that during rotation of the carousel the cam follower 19 may follow the cam track 31. The receiver 21 may press the tube against a press wall 33. The press wall 33 provides sufficient guidance for the tube 3 to clamp the tube between the wall 33 and the receiver 21. The apparatus may be provided with rotary bearings 35 and a gear wheel 37 which may be driven by a motor (not depicted).

By receiving the tube 3 close to the rotation axis 11, moving it with the carriage 17 along the guide 15 driven by a cam follower 19 to a position further away from the rotation axis 11 there is provided a spacing between the tubes, which is transferred to the second track.

Figure 4:
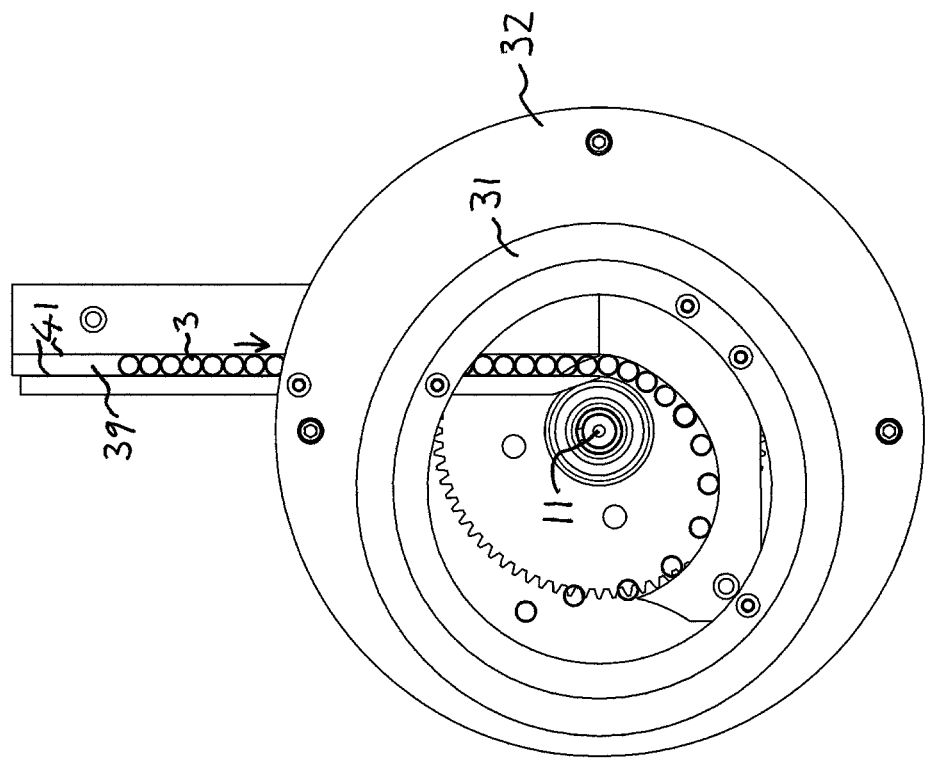
FIG. 4 depicts a top view of a portion of the adjustment apparatus with the rotary carrousel of FIGS. 2 and 3 removed.

FIG. 4 depicts a top view of a portion of the adjustment apparatus with the rotary carrousel 9 of FIG. 2 removed. The figure depicts how the stationary cam track 31 is formed in the cam track portion 32. The stationary cam track 31 is provided in a plane substantially perpendicular to the rotation axis 11 so that during rotation of the carousel the cam follower may follow the cam track 31.

The first track may comprise a channel 39 with channel walls 41 for guiding the tubes 3. The channel offers for a good guidance of the tubes to the rotary carousel.

Figure 5:
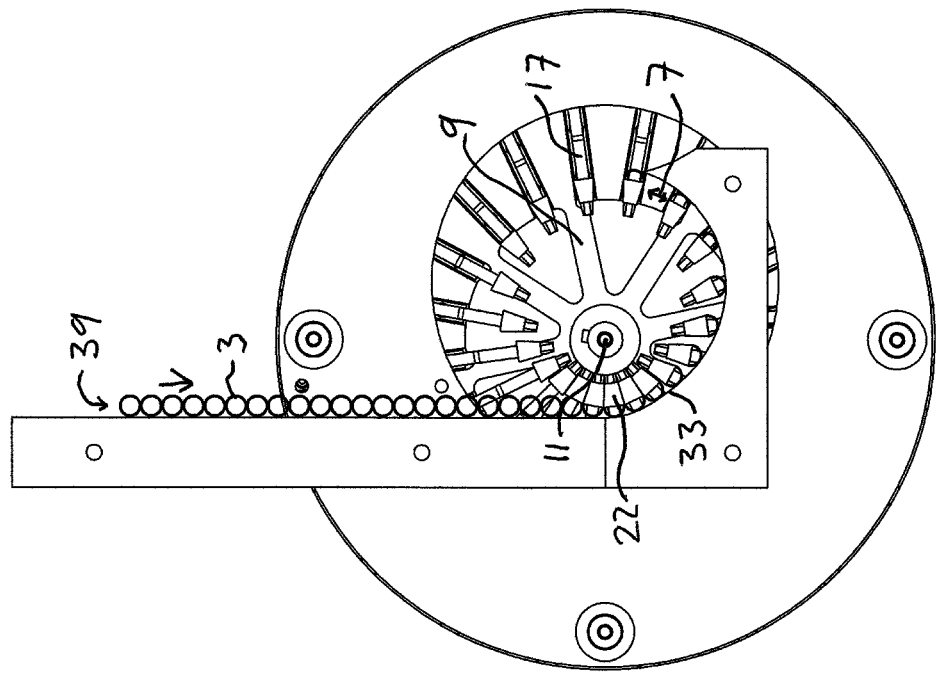
FIG. 5 depicts a bottom view of a portion of the adjustment apparatus.

FIG. 5 depicts a bottom view of a portion of the adjustment apparatus. The cam track portion 32 is well visible. Tubes 3 move through the channel 39 of the first track to the rotary carrousel 9 rotating around rotation axis 11. The tubes are taken over by the support 22 close to the rotation axis 11, moved with the carriage 17 along the guide driven by a cam follower to a position further away from the rotation axis 11 such that there is provided a spacing 7 between the tubes. Press wall 33 provides sufficient guidance for the tube 3 to clamp the tube between the press wall 33 and the receiver.

Figure 6:
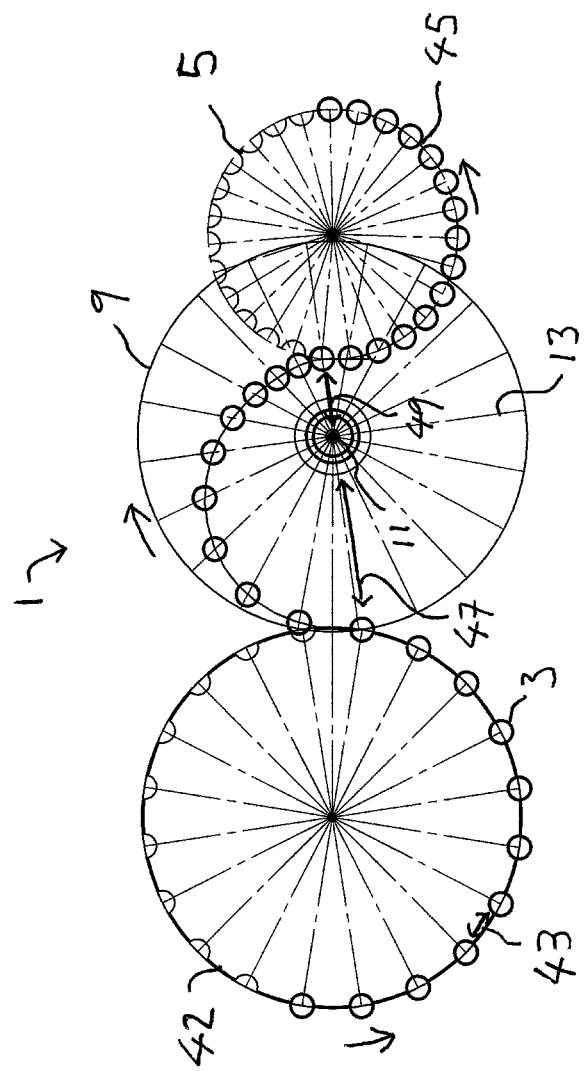
FIG. 6 depicts schematically a top view on an electronic cigarette tubes spacing adjustment apparatus according to a second embodiment.

FIG. 6 depicts schematically a top view on an electronic cigarette tubes spacing adjustment apparatus 1 according to a second embodiment which adjusts the space from relatively large to relatively small. The apparatus 1 adjusts spaces between tubes 3 received from a first track 42 with a first spacing and delivered to a second track 5 with a second spacing. For example, the apparatus 1 receives tubes 3 from a first track 42 with a relatively large spacing 43 and delivers them to a second track 5 with a small spacing 45. The first or second track may comprise rotary carrousels. The rotary carrousel of the second track 5 may take the tubes over from the rotary carousel 9 and keep the distance between the tubes constant.

The apparatus 1 comprises a rotary carrousel 9 to adjust the space between the tubes. The rotary carrousel 9 is configured to rotate about a rotation axis 11 and provided with a guide extending with the longitudinal axis partially along a line 13 substantially intersecting the rotation axis 11.

A carriage may be movably mounted to the carrousel for traveling along the guide in a reciprocating movement driven by a cam follower following a cam track while the carousel 9 is rotating identical to that in FIG. 2. A receiver may be provided to the apparatus for receiving the tube 3 with a first spacing 43 from the first track 42 at a first distance 47 from the rotation axis 11 and delivering the tube to the second track at a second distance 49 from the rotation axis 11 with a second spacing 45.

It is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

For example, the invention may relate to an electronic cigarette tubes individualiser apparatus for individualising tubes received from a first track without spacing and provided to a second track with a spacing, wherein the apparatus comprises:
a rotary carrousel configured to rotate about a rotation axis and provided with a guide extending with the longitudinal axis partially along a line substantially intersecting the rotation axis;
a stationary cam track extending around the rotation axis;
a carriage mounted to the carrousel for traveling in a reciprocating movement along the guide driven by a cam follower following the cam track while the carousel is rotating; and,
a receiver connected to the carriage for receiving the tube from the first track close to the rotation axis and delivering the tube to the second track further away from the rotation axis with a spacing.

Furthermore, the terms and phrases used herein are not intended to be limiting, but rather, to provide an understandable description of the invention.

The terms "a" or "an", as used herein, are defined as one or more than one. The term another or subsequent, as used herein, is defined as at least a second or more. The terms including and/or having, as used herein, are defined as comprising (i.e., not excluding other elements or steps). Any reference signs in the claims should not be construed as limiting the scope of the claims or the invention. The mere fact that certain measures are recited in mutually different dependent claims does not indicate that a combination of these measures cannot be used to advantage. The scope of the invention is only limited by the following claims.

The invention claimed is:

1. An electronic cigarette tubes spacing adjustment apparatus for adjusting spaces between tubes received from a first track with a first spacing and delivered to a second track with a second spacing, wherein the apparatus comprises:
a rotary carrousel configured to rotate about a rotation axis and provided with a guide extending with the longitudinal axis partially along a line substantially intersecting the rotation axis;
a stationary cam track extending around the rotation axis;
a carriage mounted to the carrousel for traveling in a reciprocating movement along the guide driven by a cam follower following the cam track while the carousel is rotating; and
a receiver connected to the carriage for receiving the tube from the first track at a first distance from the rotation axis and delivering the tube to the second track at a second distance from the rotation axis while adjusting the spacing from the first spacing to the second spacing between delivering and receiving the tube.

2. The apparatus according to claim 1, wherein the stationary cam track is provided in a plane substantially perpendicular to the rotation axis.

3. The apparatus according to claim 1, wherein the guide is provided in a plane substantially perpendicular to the rotation axis.

4. The apparatus according to claim 1, wherein the receiver is constructed and arranged to press the tube against a press wall.

5. The apparatus according to claim 1, wherein the cam follower comprises a rotary wheel.

6. The apparatus according to claim 1, wherein the first or second track comprises a rotary carrousel.

7. The apparatus according to claim 1, wherein the first or second track comprises a channel with walls for guiding the tubes.

8. The apparatus according to claim 1, wherein the apparatus is constructed and arranged to transport the tubes with their longitudinal axis parallel to the rotation axis.

9. The apparatus according to claim 1, wherein the guide extends between 2 to 25 cm from the rotation axis with the longitudinal axis along lines substantially intersecting the rotation axis.

10. The apparatus according to claim 1, wherein between the guide and the carriage a linear bearing is provided.

11. The apparatus according to claim 1, wherein the guide comprises a rail and the carriage is provided with a slide running over the rail.

12. The apparatus according to claim 1, wherein between 5 to 100 guides with carriages are provided to the apparatus.

13. The apparatus according to claim 1, wherein between 10 to 50 guides with carriages are provided to the apparatus.

14. The apparatus according to claim 1, wherein between 20 to 40 guides with carriages are provided to the apparatus.

15. The apparatus according to claim 1, wherein the apparatus is constructed to receive the tubes with the first spacing smaller than the second spacing with which the tubes are delivered.

16. The apparatus according to claim 1, wherein the apparatus is constructed to receive the tubes with the first spacing larger than the second spacing with which the tubes are delivered.

17. A method for adjusting spaces between electronic cigarette tubes, the method comprising:
- rotating around a rotation axis a rotary carrousel provided with a guide extending with the longitudinal axis partially along a line substantially intersecting the rotation axis;
- driving carriages reciprocating along the guide by a cam follower following a stationary cam track;
- receiving tubes from a first track with a first spacing between the tubes with a receiver connected to the carriage from a first track at a first distance from the rotation axis; and
- delivering the tubes to a second track with a second spacing between the tubes at a second distance from the rotation axis.

* * * * *